ns Patent
United States Patent [19]

Cariel

[11] 4,054,649
[45] Oct. 18, 1977

[54] THERAPEUTIC COMPOSITIONS AND THE TREATMENT OF LESIONS OF CONNECTIVE TISSUE

[76] Inventor: Leon Cariel, 85, rue de Sevres, 75006 Paris, France

[21] Appl. No.: 652,860

[22] Filed: Jan. 27, 1976

[30] Foreign Application Priority Data

Nov. 24, 1975 France .................... 75.35851

[51] Int. Cl.$^2$ .................... A61K 35/78
[52] U.S. Cl. .................... 424/195
[58] Field of Search .................... 424/195

[56] References Cited

PUBLICATIONS

Steinmetz, "Codex Vegetabilis", (1957), pp. 47t/m, 54, 254t/m, 263, 419t/m., 428, 429t/m, 436, 963t/m, 973, and index pp. 4, 59.

Primary Examiner—Stanley J. Friedman
Attorney, Agent, or Firm—Cushman, Darby & Cushman

[57] ABSTRACT

A pharmaceutical composition for topical application to and treatment of lesion of connective tissue by acting on fibrillar and microfibrillar structures, proelastin, and/or on the fundamental substance and its collagen, the essential active constituent being an Alchemilla extract.

6 Claims, No Drawings

THERAPEUTIC COMPOSITIONS AND THE TREATMENT OF LESIONS OF CONNECTIVE TISSUE

This invention relates to a novel phytotherapeutic product useful for restoring, repairing and reactivating the conjunctive tissue by acting on the lamellar cells or fibroblasts and/or the fundamental substance and its collagen, and exerting therefore a curative action leading to the resorption of stretch marks (grooves and discoloration) of striae gravidarum or weals or cicatrices, and to the smoothing out of wrinkles and the restoration of the arterial and vascular tissue, notably in case of arteriosclerosis.

Up to recent times the general belief was that any destruction of elastic fibres was irreparable, and therefore it was admitted that superficial wounds due to exogen factors such as linear cicatrices resulting from wounds or operations, and weals caused by an abnormal and momentary distension of the dermis, or by a pathological hormonal action, were indelible.

Similarly, it was admitted that no treatment whatsoever could regenerate or reactivate the arterial or vascular elastic tissue in order to eliminate the causes of arteriosclerosis.

It will be observed that in all these cases one is confronted with lesions affecting the conjunctive tissue which, theoretically, cannot be resorbed unless this tissue is restored, i.e. through the development of new cells.

Nowadays scientists are reduced to simple hypotheses or assumptions in the field of cell developments.

The American biologist Paul Weiss suggested a pattern for regulating the development of cells by virtue of an inhibiting factor. Two Englishmen, Bullough and Laurence, made experimental researches on the dermis which evidenced the fact that the dermis contains an extremely complicated chemical substance capable of inhibiting mitoses, the concentration of this substance decreases in the vicinity of a pathological injury, this intracellular inhibitor (for which the name of Chalonne was proposed) inherent to each tissue, being probably synthetized by the epiderm. Now, this epidermic inhibitor has apparently been isolated and would consist of a glycoprotein having a molecular weight in the range of 30,000 to 40,000.

It is not excluded that a second mechanism be superposed to the first one and that a humoral extracellular factor might have a stimulative action.

DETAILED DESCRIPTION

The Applicant found that Alchemilla, whether utilized alone or in admixture with other vegetable extracts, was capable of exerting a useful action on any lesion made to the conjunctive tissue in connection with an alteration of variable (for example physiological or pathological) nature or origin of the macromolecules of the intercellular matrix and of their structural organization.

Among these lesions, striae, weals, cicatrices due to a restoration of the sub-cutaneous conjunctive tissue subsequent to a wound, dystrophias entailing the formation of wrinkles and cutaneous ageing, localized lipodystrophias or cellulitis may be cited, inter alia.

Considering the uncertainties of the actual process involved in the development of human tissue cells, it is rather surprising that very positive results have been obtained through the simple use of a galenic product, namely "Alchemilla arvensis", of which certain functions are already known, such as astringent, haemostatic and vulnerary functions when this product is administered as a drug for external use, in addition to its depurative, emollient and diuretic functions when it is absorbed by the oral route (Codex Vegetabilis, F. K. Steinmetz, 1957 Edition).

The action exerted by Alchemilla on the development of conjunctive tissue cells is not ascribable to anyone of the hithertoknown properties of this substance since said action is effective on fibroblasts, on the fundamental substance and/or on the elastase and is either capable of stimulating the lysine-oxidase or inhibiting the elastase.

In the following disclosure, the terms "fibrillar structures" is applied incorrectly, in addition to the fibrillary and microfibrillary network proper, to fibroblats, to the fundamental substance and to its collagen.

the various species of Alchemilla are adequate for the purpose but the use of "Alchemilla arvensis" is preferred.

Alchemilla is used in the form of concentrated extracts obtained from fresh leaves, stems and stalks of Alchemilla by using non-destructive processes performed in the cold state (for example by maceration at about 40° C) according to the vehicle employed; these methods yield Sorbitolisates, Conapsates, Oleates, Glycerisates, Glycolisates (with polyglycols, propyleneglycols, di- or tripropyleneglycols), hydroglycolisates, hydroalcoholisates, d'Alchemilla such that 1 kilogram of fresh leaves stems or stalks of Alchemilla will yield five kg of liquide extracts of Alchemilla.

In the following description the terms "hydroglycolic extract" refers to liquid extracts thus obtained by treating leaves and stems of Alchemilla in a 50/50 mixture of propylene-glycol and water.

This hydroglycolic extract corresponds for example to those sold under the Trade Name "Phytelenes" by les Laboratoires Galeniques VERNIN (77002 Melun, France) and registered by the Food and Drug Administration CRMCS under the No. 00 12347.

When the extract is solid 1 kg of powder of dry extract of Alchemilla corresponds to 100 kg of fresh leaves, stems or stalks.

Of course, other forms of administration may be contemplated, such as buccal, parenteral, rectal route, etc. provided that the sideeffects inherent to those modes of administration are compensated by using inhibiting or compensating additives.

A liquid product available for per-cutaneous treatment or parenteral administration may be:

Example n° 1
| | |
|---|---|
| Hydroglycolic Alchemilla extract (phytelene) | 6 gr. |
| Solution of Propyleneglycol 50 % | 1 ml |
| Distilled water 50 % | |
| Sodium dioctyl sulfo-succinate | 0,05 ml |

Example n° 2
| | |
|---|---|
| Mother alcoholic tincture of Alchemilla | 6 gr. |
| A solution consisting of: 50 % Propyleneglycol and 50 % Distilled water | 1 ml |
| A hydroalcoholic solution of sodium dioctyl sulfo-succinate | 0,05 ml |

Example n° 3

In the gel form the product comprises:

-continued

| | |
|---|---|
| hydroglycolic Alchemilla extract | 25 gr |
| Gelatinizer (such as Carbopal 940) | 0,50 gr |
| Pure triethanolamine | 0,50 gr |
| Nipogine | 0,030 gr |
| Purified water | 74 gr |

EXAMPLE No. 4

In the cream form the product comprises:
25 to 30 gr of hydroglycolic Alchemilla extract
for 75 to 70 gr of conventional excipient as lanolin and vaselin.

A solid product available for buccal way may be:
Capsule or tablet of 50 mg of dry extract of Alchemilla.

Clinical treatment

EXAMPLE A: Treatment of Stretch Marks

The liquid product of examples 1 or 2 is rubbed with the finger tips into the skin in the effected area.

Five ml. of the composition of formulation above, was applied daily to the area of stretch marks by applying topically to the affected area of the patient. This was conveniently accomplished by providing the patient with a 5 ml. quantity of the formulation with instructions to massage using the fingertips into the affected skin area. This treatment was continued once a day for a period of 3 weeks, at which time the stretch marks began to lose some of their characteristic color and, little by little, shrink in width and length.

Duration of treatment depends upon a number of factors including the age of the patient, the age of the lesion and frequency of application. Generally, the treatment continues for at least 1 to 3 months. At the end of the first month I have observed that the stretch marks are resorbed in the form of a thin line which is only slightly visible. If treatment is continued for more than 1month, topical composition is preferably applied every other day.

EXAMPLE B (Treatment of arteriosclerosis by parenteral way)

One injection of 10 ml of the liquid product of Example No. 1 1 out 2 days during 3 months.

EXAMPLE C (Treatment of arteriosclerosis by buccal way)

One capsule or tablet of 50 mg 2 times per day during 3 months.

In the treatment of arteriosclerosis if an diuretic or depurative action is remarked, patient can complete the treatment by Alchemilla with absorption of a known inhibiting or compensating additives of said actions.

CLINICAL TRIALS

First case:
Little girl 13 years ago.
Many covergent striae around each nipple (length: 3 cm, width 2 mm - color pale pink, ancientness: 1 year.
Cause: Sharp inflating of breast at the time of puberty.
Treatment: by rubbing of the affectevareas with 5 ml of the product of example No. 1 2 times per day.
Results after treatment of 1 month:
  General appearance: ameliorated
  Number of striae: without change
  Length of striae: without change
  width: ½ mm.
  colour: same color as the surrounding skin.
Second case:
Woman 32 years ago.
affected areas: Buttocks
Striae:
  length: 2 to 5 cm.
  width: 2 to 6 mm
  colour:
  small striae: white
  large striae: pink
Ancientness: 10 years ago
Cause: increase of weight
Treatment: as first case
Results after treatment of one month:
  general appearance: ameliorated
  number of striae: without change
  length of striae: without change
  width of striae: the more large: without change
  The least large: decreased
Colour: the old white striae: without change the old pink striae: white
Conclusion:
  Action on the more large: on the color only
  Action on the least large: on the width.
Other cases:
  In the cases of very old striae a treatment of 1 month has only an action on the colour.
  If the treatment is renewed during 3 months the width of striae decreases and striae become linear.
  No trials have been sufficently long for knowing the result of a treatment of 1 year on the length of striae.

The applicant also associated Alchemilla with other extracts, notably Horsetail (Equisetum arvensis), a plant having a high content of silicon in the protoplasmic colloidal form, i.e. the only one assimilable by the human organism.

The intermolecular bridges are primarily composed of silicon as had already been suggested by the considerably earlier studies, particularly those of M. and J. Leoper, showing the abundance of normal elastic tissue in silicon. Even further, as the recently published and very precise works in this regard indicate, i.e., for example, Klaus Schwartz, Proc. Nat. Acad. Sci. USA May 1973.

Besides its structural importance, noted above, silicon plays an essential role in the fibrocytic metabolism phenomena particularly at the level of enzymatic mechanisms where it intervenes as a co-enzyme.

The applicant, basing himself on the fact that silicon is capable of stimulating the reactivation of elastic fibres from indifferenciated fibroblasts, thought of associating Horsetail with Alchemilla in a novel product tending to increase the silicon content of the dermis.

Whereas the effect produced by silicon is observed only after a relatively long time period, the clinical tests performed as discussed hereinafter proved that the effects of Alchemilla and Horsetail tend to combine with each other and to become more rapid.

By adding Climbing Ivy (Hedera Helix) extract to these substances a surprising synergetic effect is obtained, which is difficult to explain otherwise than through neurotissulovascular reactions, notably oestrogenic reactions, of the Ivy components.

Of course, Horsetail and Ivy extracts are used in the same form that Alchemilla in liquid extracts as hydroglycolic extracts consistent with the definition given hereinabove for Alchemilla.

The Applicant used notably "phytelenes" from the above-mentioned Vernin Laboratories, Horsetail and Ivy such as registered by the Foods and Drugs Administration CRMCS under the Nos. 0012045 and 0011461, respectively.

EXAMPLES

Formulation No. 1
The liquid product includes by weight:
Hydroglycolic Alchemilla extract — 60
Hydroglycolic Equisetum extract — 30
Hydroglycolic Hedera Helix extract — 10
Formulation No. 2
The liquid product includes by weight:
  Pure alcoholic tincture of Alchemilla — 4 gr
  Alcoholic extract of Hedera Helix — 1 gr
  Alcoholic extract of Equisetum — 2 gr
  in a solution of:
  Propyleneglycol 50% — 1 ml
  Distilled water 50%
  Sodium dioctyl sulfo-succinate — 0,05 ml
Formulation No. 3
In the gel form the product contains:
  Formulation of sample no. 1 — 25 gr
  Gelatinizer (Carbopol 940) — 0,5 gr
  Pure triethalonamine — 0,5 gr
  Nipagine — 0,030 gr
  Purified water — 74 gr
Formulation No. 4
In the cream form the product contains:
  Formulation of sample no. 1 — 25 to 30 gr
  Excipient (lanolin and vaselin) — 75 to 70 gr
Formulation No. 5
From Codex Liquid extracts:
  Pure Alcoholic tincture of Alchemilla — 4 g
  Fluid alcoholic extract of Hedera Helix — 1 g
  Fluid alcoholic extract of Equisetum — 2 g
  Ethyleneglycol ester (Transcutol) — 1 ml
  Hydroalcoholic solution of sodium dioctyl sulfo succinate
  (Manoxol OT) 2% in a mixture distilled water — 0,05 ml
  Alcohol at 90%
Formulation No. 6
From liquid concentrated hydroglycolic vegetable extracts
  (1 kg fresh plant gives 5 kg of liquid extract) — parts by weight
  Alchemilla extract — 30,35
  Hedera Helix extract — 14,20
  Equisetum extract — 40,45
  Pharmaceutically acceptable solvent — 15

Clinical treatment

The clinical treatment and the dosage are the same as in the preceding cases, the product had the formulation No. 6.

Clinical trials

The results of the treatment were eveluated on the base of the following parameters: length, width, and colour of the striae, appearance of the skin, development of additional striations.

First group of trials
-preventive treatment beginning the sixth month of pregnancy and continuing to term
-25 pregnant women without signs of striae gravidarum (15 primigravidas and 10 plurigravidas).

The mere preventive treatment in 25 cases showed the following results:
23 women had no striae at term,
2 women had developed striae in spite of the treatment. The lesions observed were limited in number, located in the breast and abdominal area, max. 3mm in length and width, colour pink.

Second group of trials
Curative treatment of existing striae during pregnancy:
35 pregnant women (20 primigravidas, 15 plurigravidas).
Results:

| A) Primigravidas: | | | |
| Parameters | Exacerbated | Unchanged | Improved |
| --- | --- | --- | --- |
| length | 2 | 8 | 10 |
| width | 2 | 10 | 8 |
| Colour | 2 | 6 | 12 |
| new striae | | | |
| B) Multigravidas: | | | |
| Parameters | Exacerbated | Unchanged | Improved |
| Length | 1 | 10 | 4 |
| width | 1 | 8 | 6 |
| colour | 0 | 10 | 5 |
| new striae | 1 | | |

Third group of trials

Curative treatment of striae after delivery 20 pregnant women (12 primiparas - 8 pluriparas) duration: one month

| A) Primiparas | | |
| Parameter | Failure | Improvement |
| --- | --- | --- |
| Length | 6 | 6 |
| Width | 5 | 7 |
| colour | 1 | 12 |
| wrinkles | 2 | 10 |
| B) Pluriparas: | | |
| Parameter | Failure | Improvement |
| length | 8 | 0 |
| width | 6 | 2 |
| colour | 2 | 6 |
| wrinkles | 8 | — |

Conclusion

The product comprising the three extracts (Alchemilla, Equisetum, and Hedera) gives good results in preventive treatment and in curative treatment of primigravidas having striae and of primiparas' striae.

The action is least obvious in the case of curative treatment of plurigravidas having striae.

the same product is more inefficacious in the case of treatment of striae of pluriparas.

These results seem less good than the results of the trials using Alchemilla extracts only.

This comparison between results proves that Alchemilla is the plant the more active.

What is claimed is:

1. A therapeutic method for the treatment of stretched and discolored conjunctive tissue lesions or stretch marks associated with pregnancy comprising applying topically to the affected area of a woman exhibiting such lesions a therapeutic amount of a pharmaceutical composition containing, as active ingredients in weight percent:
Alchemilla extract — 30–80%
Equisetum extract — 50–10%

Hedera Helix extract — 20-10% the total of said extracts being 100 weight percent, and continuing such treatment for a period of time until said lesions have been at least partially improved.

2. A therapeutic method for the treatment of lesions of conjunctive tissue comprising applying to the affected area of a person requiring such treatment a therapeutic amount of Alchemilla extract and continuing said application until the subcutaneous conjunctive tissue is substantially restored.

3. The therapeutic method of claim 2 wherein the extract is *Alchemilla arvense extract*.

4. A therapeutic method for the treatment of stretched and discolored conjunctive tissue comprising applying to the affected area of a person requiring such treatment a therapeutic amount of Alchemilla extract and continuing said application until the sub-cutaneous conjunctive tissue is substantially restored.

5. The therapeutic method of claim 4 wherein the extract is *Alchemilla arvense extract*.

6. A topical pharmaceutical composition for direct application to and treatment of the lesions of connective tissue including, as the pharmaceutically active ingredients in percent by weight, the following hydroglycolic extracts:

Alchemilla extract 30-80%
Equisetum extract 50-10%
Hedera Helix extract 20-10% the total of said extracts being 100 weight percent, the extracts contained in a solution of equal parts of propylene glycol and distilled water.

* * * * *